United States Patent [19]
Unger

[11] Patent Number: 5,997,299
[45] Date of Patent: Dec. 7, 1999

[54] ANCHOR FOR DENTAL IMPLANTS AND DEVICE FOR THE ALIGNMENT OF THE ANCHOR

[76] Inventor: Heinz-Dieter Unger, Kommenderiestrasse 124, D-49080 Osnabrueck, Germany

[21] Appl. No.: 09/011,975

[22] PCT Filed: Mar. 17, 1997

[86] PCT No.: PCT/EP96/03784

§ 371 Date: Feb. 20, 1998

§ 102(e) Date: Feb. 20, 1998

[87] PCT Pub. No.: WO97/09004

PCT Pub. Date: Mar. 13, 1997

[30] Foreign Application Priority Data

Sep. 1, 1995 [DE] Germany ......................... 295 14 042 U

[51] Int. Cl.[6] .................................................. A61C 8/00
[52] U.S. Cl. .......................................... 433/173; 433/72
[58] Field of Search ................................. 433/72, 74, 75, 433/76, 172, 173

[56] References Cited

U.S. PATENT DOCUMENTS

| | | | |
|---|---|---|---|
| 1,189,753 | 7/1916 | Thue | 433/76 |
| 1,216,596 | 2/1917 | Nishi | 433/75 |
| 4,832,601 | 5/1989 | Linden | 433/173 |
| 5,073,110 | 12/1991 | Barbone | 433/173 |
| 5,133,662 | 7/1992 | Metcalfe | 433/173 |
| 5,215,460 | 6/1993 | Perry | 433/173 |
| 5,302,125 | 4/1994 | Kownacki et al. | 433/172 |
| 5,516,288 | 5/1996 | Sichler et al. | 433/173 |
| 5,564,922 | 10/1996 | Rosa et al. | 433/173 |
| 5,667,384 | 9/1997 | Sutter et al. | 433/173 |
| 5,695,334 | 12/1997 | Blacklock et al. | 433/75 |

FOREIGN PATENT DOCUMENTS 288702 11/1988 European Pat. Off. .

*Primary Examiner*—John J. Wilson
*Attorney, Agent, or Firm*—Jordan and Hamburg LLP

[57] ABSTRACT

An anchor for a prosthetic superstructure which can be connected with an implant includes a mounting part having threads engageable with the implant and a connecting piece supported on the mounting part for connecting with an anchor head for a dental prosthesis, the mounting part including a partial spherical space which accommodates the connection piece. The partial spherical space has a partial spherical wall, the mounting part further including a threaded pasage and a threaded member threaded in the threaded passage and fixing the connecting piece on the mounting part in an aligned disposition.

21 Claims, 5 Drawing Sheets

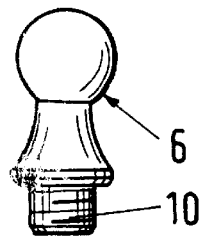
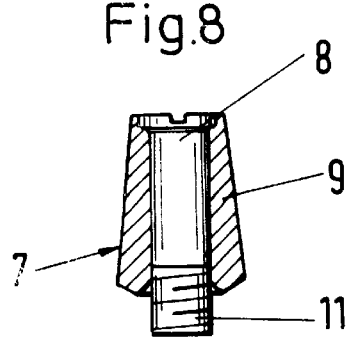
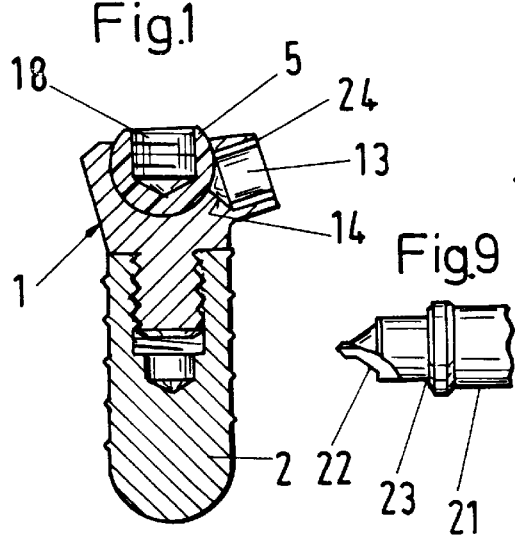
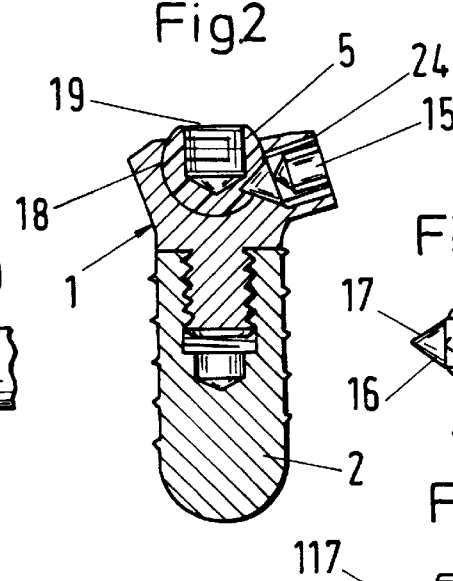
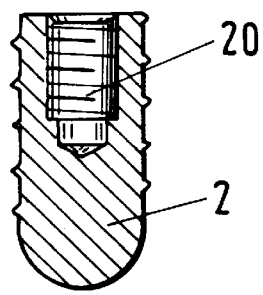
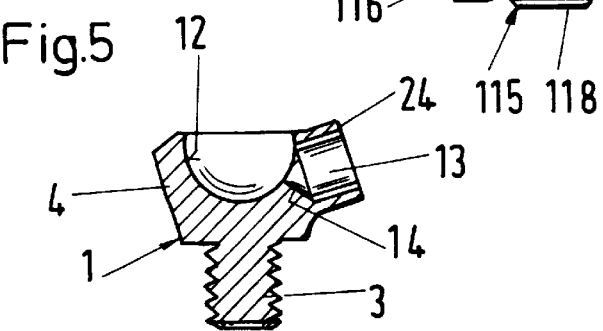
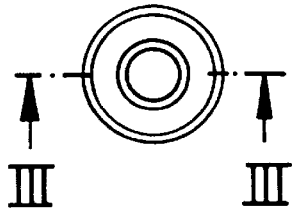
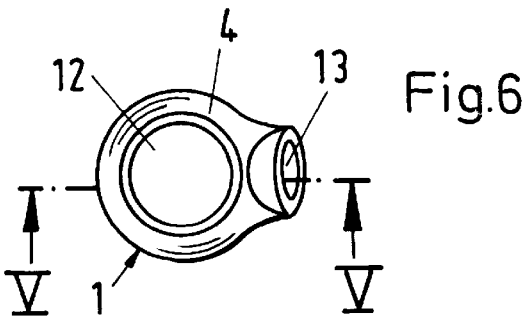

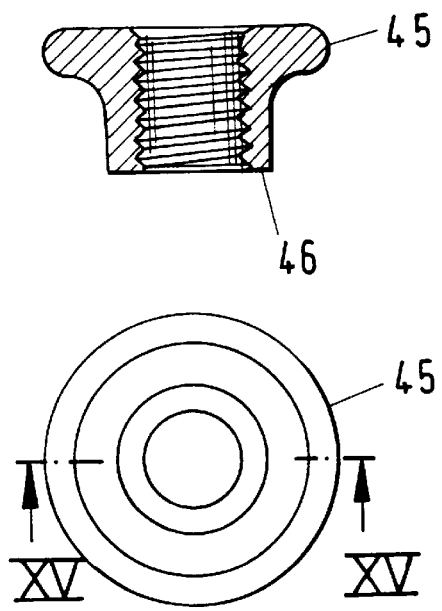
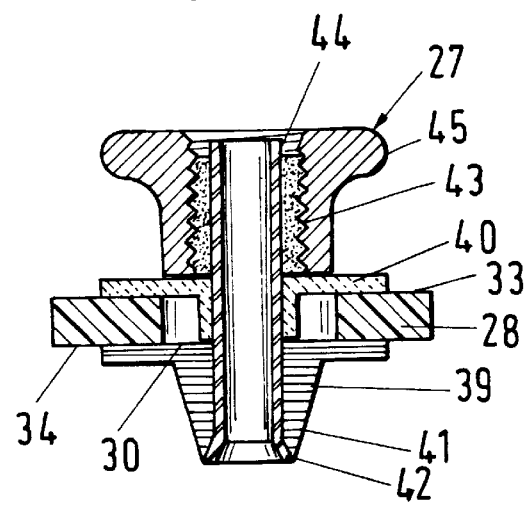
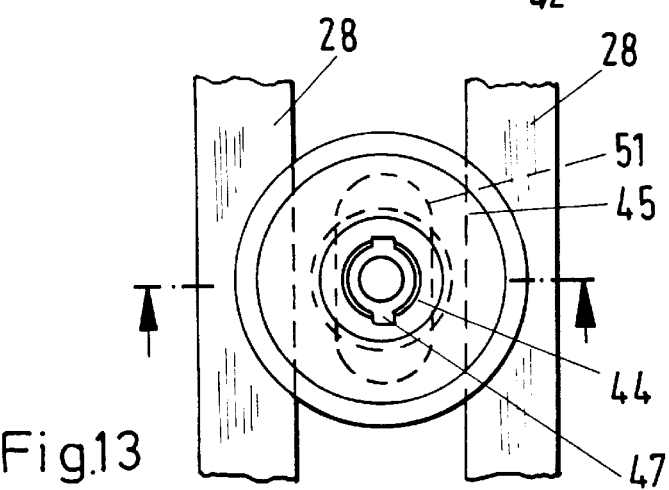
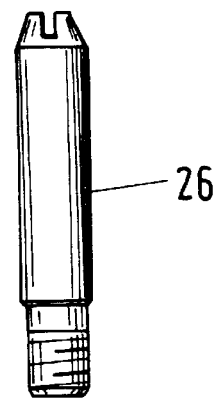

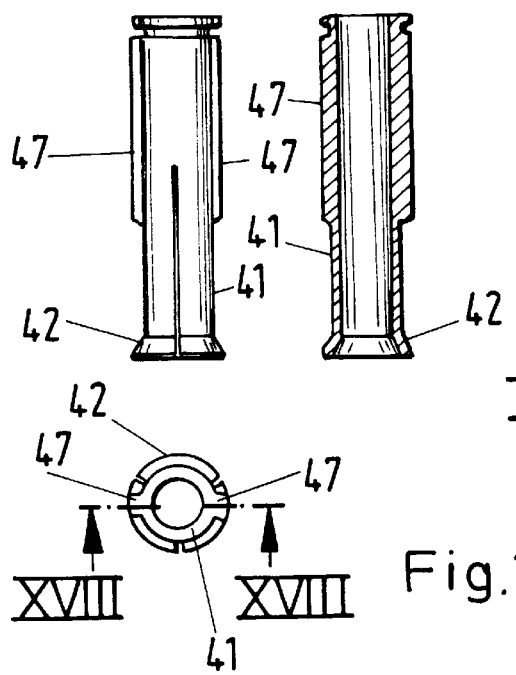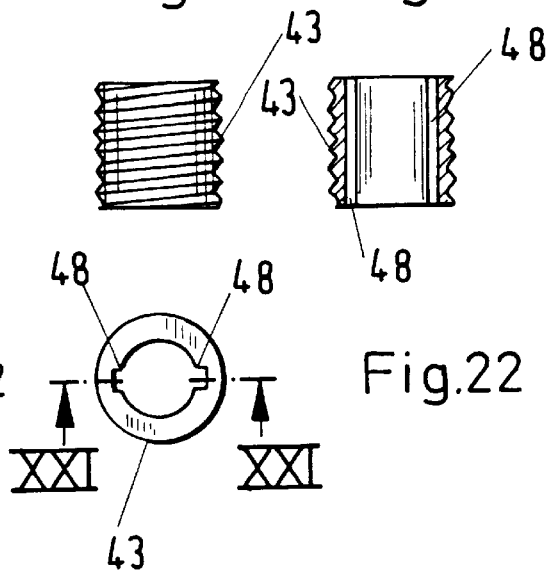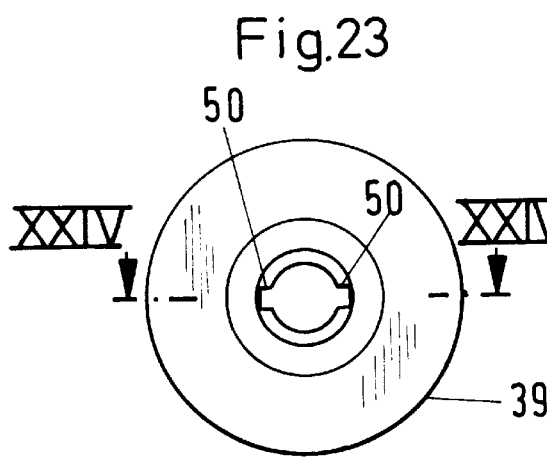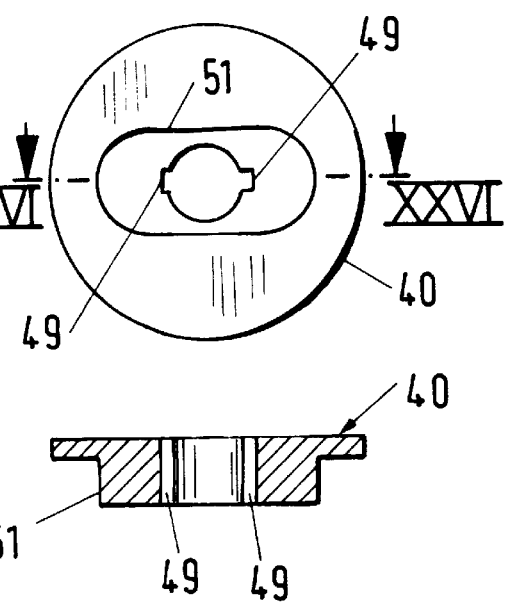

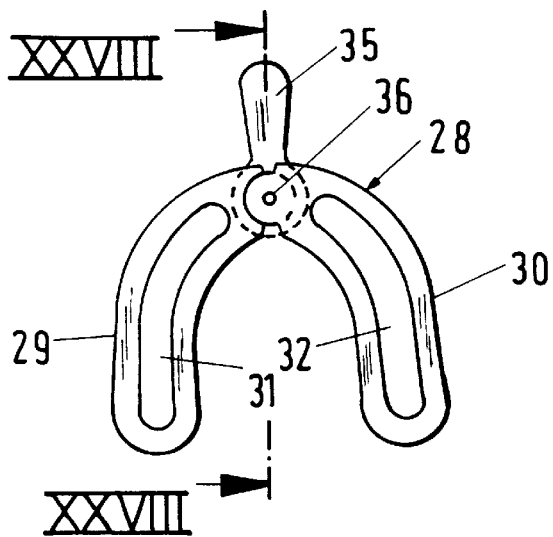
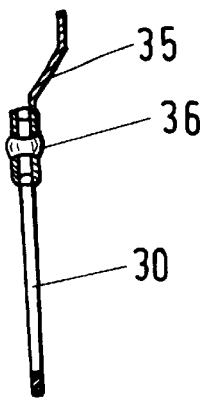
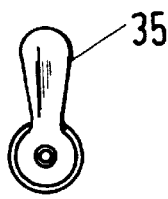
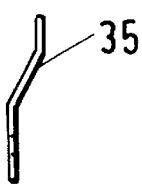
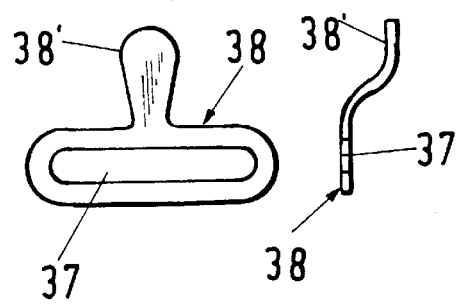
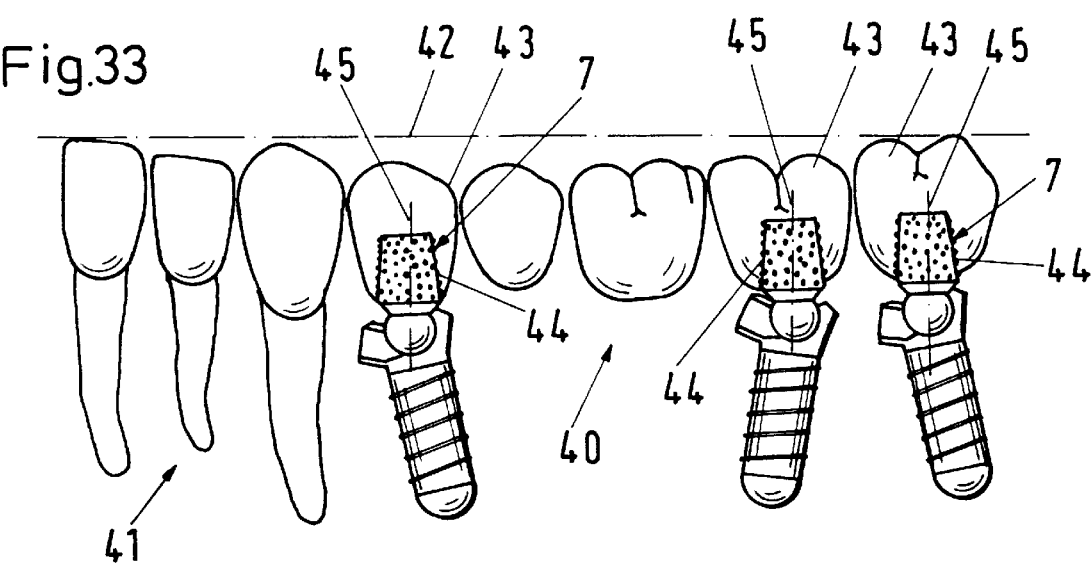

5,997,299

ANCHOR FOR DENTAL IMPLANTS AND DEVICE FOR THE ALIGNMENT OF THE ANCHOR

The invention relates to an anchor for prosthetic supraconstructions which anchor can be connected with an implant, as well as to an apparatus for aligning the anchor and to a supraconstruction, which can be connected with the anchor.

BACKGROUND OF THE INVENTION

For anchoring dental prostheses, spheres, crowns or similar anchoring heads are used, which are screwed directly into the implant, which is provided at its upper side with a coaxial connecting borehole with internal thread and are aligned coaxially with the implant. If, for reasons specific to a jaw, the implants for supporting dental prostheses cannot be aligned axially parallel to one another, compensatory measure must be taken and compensatory means used, in order to ensure that the prosthesis is seated satisfactorily and/or handled precisely when put in place and when removed. For this purpose, attachments between all diverging units are used in the case of fixed supraconstructions, whereas, for removable constructions, special secondary crown parts are used which have to be made especially and, after being put in place on their associated primary crowns, must compensate for their divergences. Because of the individual adaptation, such compensatory measures and means are exceptionally labor-intensive and costly and, moreover, represent a burden for the patient because of the frequency of the appointments that are necessary. Furthermore, in the case of attachments, there are always microgaps which permit movements which, from the point of view of a firm support for the implant, are undesirable.

SUMMARY OF THE INVENTION

It is an object of the invention to simplify the compensatory measures and means required to correct the necessarily diverging alignment of implants in the jaw and, with that, to shorten the time required for such measures and means and to make them less expensive.

The inventive adapter, which can be premanufactured industrially, provides an exceedingly simple possibility for the desired alignment of an anchoring head, independently of the alignment of an implant, and makes attachments and individually manufactured secondary crown parts superfluous. The alignment can be made exceedingly rapidly and, at the same time, precisely with the help of the inventive aligning device as a result of which the burden on the patient is reduced to one appointment. The inventive supraconstruction, in turn, can be premanufactured industrially and can be handled less expensively and more easily, because time-consuming dental measurements do not have to be made.

Numerous further advantages and details arise out of the following description and the drawing, in which an example of the object of the invention is illustrated in greater detail.

IN THE DRAWINGS

FIG. 1 shows an inventive adapter, inserted in an implant, in longitudinal section, FIG. 2 shows a representation similar to that of FIG. 1, with a fixed connection piece, FIG. 3 shows an individual representation of the implant in a section along the line III—III of FIG. 4, FIG. 4 shows a plan view of FIG. 3, FIG. 5 shows a representation of the adapter in a section along the line V—V of FIG. 6, FIG. 6 shows a plan view of FIG. 5, FIG. 7 shows a representation of ball head part, which can be connected with the adapter of FIG. 5.

FIG. 8 shows a representation of a crown head part, which can be connected with the adapter of FIG. 5, FIG. 9 shows a truncated view of a drill for drilling a fixing hole in the connection piece of the adapter, FIGS. 10a and 10b show views of fixing screws for fixing the connection piece in the mounting of the adapter, FIG. 11 shows a representation of the inventive aligning device, FIG. 12 shows an individual representation of an aligning element of the aligning device of FIG. 11 in longitudinal section, FIG. 13 shows a truncated plan view of FIG. 12, FIG. 14 shows a view of an aligning pin, which can be connected with the connection piece of the adapter and acts together with an aligning element, FIG. 15 shows a representation of the adjusting nut in section along the line XV—XV of FIG. 16, FIG. 16 shows a plan view of FIG. 15, FIG. 17 shows a side view of the clamping sleeve of the aligning element of FIG. 12 in a single representation, FIG. 18 shows a section through the clamping sleeve along the line XVIII—XVIII of FIG. 19, FIG. 19 shows a plan view of FIG. 18, FIG. 20 shows a side view of the aligning element bushing with the external thread of FIG. 12, FIG. 21 shows a section through the bushing with the external thread along the line XXI—XXI in FIG. 22, FIG. 22 a plan view of FIG. 21, FIG. 23 shows a plan view of the lower parallelizing body of the aligning element of FIG. 12, FIG. 24 shows a section along the line XXIV—XXIV of FIG. 23.

FIG. 25 shows a view of the upper parallelizing body of the aligning element of FIG. 12 from below, FIG. 26 shows a section along the line XXVI—XXVI of FIG. 25, FIG. 27 shows a plan view of an aligning template of the aligning device of FIG. 11, FIG. 28 shows a section along the line XXVIII—XVIII of FIG. 27, FIGS. 29 and 30 show side views of the handle part of the aligning template of FIG. 27, and FIGS. 31 and 32 show views of a modified aligning template, and FIG. 33 shows a diagrammatic representation of an inventive supraconstruction in a diagrammatic side view of the lower row of teeth of a final set of teeth.

DESCRIPTION OF THE PREFERRED EMBODIMENTS

Figure 11:
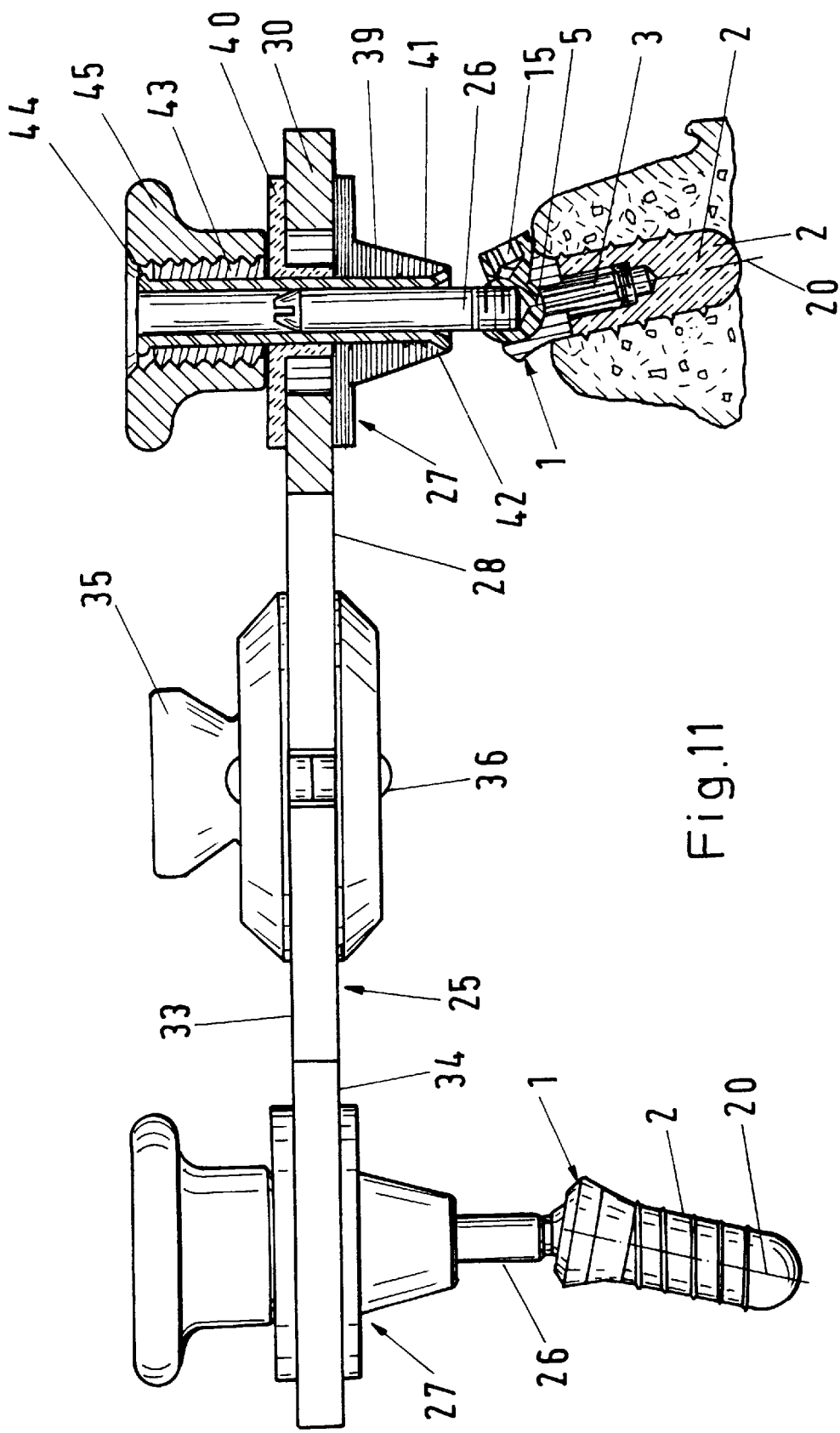

The anchor shown in the drawing for prosthetic supraconstructions, such as dental prostheses, consists essentially of an adapter 1, which comprises an mounting 4, which can be screwed by means of a pin 3 with an external thread into an implant 2, and a connection piece 5, which is supported alignably in the mounting 4, and of an anchor head part 6 for dental prostheses, which can be connected with the connection piece 5 and can be constructed as a ball head part 6 or as a crown head part or cone head part 7, formed from an occlusion screw 8 and a cone cap 9, or may have any other convenient construction. In each case, the anchor head part 6, 7 can be screwed by means of the externally threaded pin 10 or 11 into the connection piece 5 of the adapter 1.

The mounting 4 has a spherical space 12, for accommodating the connection piece 5 and comprises a lateral sunk borehole 13 with internal thread, which has an pointedly conical bottom 14 intersecting in regions with the wall of the accommodating space 12. The imaginary point of the bottom 14 of the sunk borehole 13 lies in the spherical accommodating space 12. as shown in FIG. 2. which reproduces a fixing screw 15, which is screwed into the sunk borehole 13 and has a pointedly conical end 16, which can be placed flush against the bottom 14 of the sunk borehole 13 and the point 17 of which coincides with the imaginary point of the bottom 14 of the sunk borehole 13. Alternatively, instead of a fixing screw 15 with an internal hexagonal head, a fixing screw 115 with a wrench shoulder 118, which can be broken off at a predetermined breaking plane, can also be used. After the break surface is ground and polished, such a fixing screw 115 (FIG. 10b) which, with regard to the end part 116 with the point 117, corresponds to the internal hexagonal head version 15 (FIG. 10a), occupies the sunk borehole completely.

The connection piece 5 has the outer shape of a spherical segment and is provided with a connecting borehole 18 with internal thread, the axis of which extends perpendicular to the sectional plane 19. The connection piece 5 is supported in the mounting 4, in which it can be shifted to a limited extent in all directions, and is fixed by the fixing screw 15 in the desired alignment of its axis to the axis 20 of the implant 2. The connection piece 5, more than half of which is accommodated in the mounting 4, can be pressed into the mounting 4, so as to lock into place there. However, the possibility also exists of reshaping the upper edge region of the accommodating space 12 inwards after the connection piece 5 is introduced into this space, in order to fix the connection piece 5 in the mounting 4.

As soon as the connection piece 5 assumes its desired position by means of an aligning process, the details of which will be described below, the connection piece 5 is drilled open with the help of a drill 21 with a pointedly conical drilling head 22, which is introduced through the sunk borehole 13. That part of the pointedly conical bottom 14 of the sunk borehole 13, which intersects with the wall of the accommodating space 12, is drilled out in this connection piece 5. The shoulder 23 at the drill 21 ensures the exact drilling depth, which is reached, when the shoulder 23 lies against the outer surface 24 of the mounting 4, which surrounds the sunk borehole 13. After the drill 21 is removed and the fixing screw 15 is screwed in, the pointedly conical end 16 of the fixing screw 15 comes into contact with the bottom 14 of the sunk borehole 13 and of the corresponding drilled-out part in the connection piece 5, with the consequence that this connection piece 5 is fixed precisely in the aligned position.

To facilitate the alignment process, the inventive aligning device 25, shown in FIG. 11, is used. In FIG. 11, the inventive alignment device 25 is illustrated in use with two adapter devices 1 in the implant 2. However, it can also be used with more than two adapter devices intended for the common support of a dental prosthesis. The implants 2 are illustrated with mutually diverging axes 20 in the space. Anchor head parts 6 or 7, screwed directly into the implants 2, would assume an alignment, for which their axis coincides with the axis 20 of the implant 2.

Parallel alignment of the anchor head parts 6, 7, which together support a dental prosthesis, is optimum for the seating and the handling of a dental prosthesis. In order to achieve such an alignment, aligning pins 26 (FIG. 14) are first of all screwed into the connecting boreholes 18 of the connecting pieces 5 and, moreover, at a time, at which the connecting piece 5 in the mountings 4 of the adapter 1 have not experienced any alignment or fixation yet. After that, an alignment element 27 of the aligning device 25 is placed on each aligning pin 26 and the aligning elements 27 are aligned and fixed at an aligning template 28 of the aligning device 25, as a result of which all aligning pins 26 are aligned axially parallel to one another. At the same time, the aligning pins 26 are fixed in the clamping sleeve, which is compressed in the region of its lower end by the clamping process. After that, a hole is drilled into the connection pieces 5 in the adapters 1 with the drill 21 and the fixing screws 15 are inserted, after which the aligning process for the connection pieces 5 is concluded. The aligning device 25 is then taken off and, after removal of the aligning pins 26, anchor head parts 6 or 7 are screwed into the connection pieces 5, by means of which anchors are now formed, the head parts of which are aligned precisely with one another with parallel axes.

The embodiment of an aligning template 28, shown in FIGS. 27 and 28, has an arc-shaped flat configuration, which approximately follows the course of a jaw and is provided at least in its side regions 29. 30 with an advantageously central longitudinal slot 31 or 32. The upper side 33 and underside 34 of the aligning template 28 are mutually parallel aligning surfaces, at which, at selectable positions arising from the positions of the adapters 1 in the jaw, the aligning elements 27 of the aligning device 25 can be aligned and clamped.

The aligning template 28 consists of two halves, which are hinged together and can be swiveled to fit the course of the jaw.

The half parts 29, 30 of the aligning template 28 are hinged to a handle 35, by means of a pin 36, which defines a common swiveling axis and, moreover, presses the parts 29, 30 against one another, in order to define a resistance to change. Instead of a common hinge connection with the handle 35 for the two half parts 29, 30 of the aligning template 28, there is also the possibility of mounting the parts 29, 30 in each case separately from one another on a handle provided with an elongated hole. In the latter case, the half parts 29, 30 advisably are supported in the region, in which they are connected with the handle, so that they can be moved along the elongated hole. Instead of the arc-shaped construction of the aligning template 28, the latter can also have the configuration of FIGS. 31 and 32, in the case of which a straight slot 37 for aligning the connection pieces 5 by not more than two anchors is provided in a straight base 38 with a handle 38'.

In particular, the aligning elements 27 of the aligning device 25 comprise a lower parallelizing part 39, which can be aligned with its upper side at the underside 34 of the aligning template 28, and an upper parallelizing part 40, which can be aligned with its underside at the upper side 33 of the aligning template 28. A clamping sleeve 41, slotted in the lower part, into which the aligning pin 26 can be introduced from below and clamped precisely, penetrates the two parallelizing parts 39, 40. The clamping sleeve 41 has a lower end 42, which is constructed as a stop for the lower parallelizing part 39, is constructed advisably as a conical expansion and accordingly exerts a centering effect. In particular, however, when the adjusting nut 45 is tightened, the conical expansion 42 leads to a decrease in cross section in the region of the slotted sleeve part, by means of which the aligning pin is fixed.

A bushing 43, with an external thread, is mounted so that it cannot rotate on the clamping sleeve 41 in the region above the upper parallelizing part 40. It is secured by means of a retaining ring 44 against being pulled off in the axial direction. An adjusting nut 45 can be screwed onto this external thread of the bushing 43. In the course of being screwed on, the adjusting nut 45 comes to lie with its underside 46 on the upper side of the upper parallelizing part 40 and, in so doing, clamps the parts 39, 40 and 43, as well as 26 and 41 together. Advisably, the adjusting nut 45 is constructed as a knurled-head nut and thus can be actuated by hand.

The clamping sleeve 41 is provided with external longitudinally-aligned stop springs 47, in order to support the parts 40 and 43 and, optionally, also 39, so that they cannot rotate or twist on the clamping sleeve 41. For this purpose, the parts 40, 43 and 39 are provided with appropriate locking grooves 48, 49 and 50. However, for the embodiment of the clamping sleeve 41 shown, the length of the stop springs 47 is such that the lower parallelizing part 39 is supported so that it can rotate or twist freely on the clamping sleeve.

The upper parallelizing part 40 of the aligning element 27 has a central shoulder 51, which protrudes downwards into the longitudinal slot 31 or 32 of the aligning template 28 and which has an extended, elongated hole-like peripheral contour and, in the direction of its longitudinal extent, a length, which exceeds the width of the longitudinal slot 31 or 32 in the aligning template. This makes it possible to place the shoulder 51, during the aligning process, against the bounding surfaces of the associated elongated slot 31 or 32 and to secure it against further rotation or twisting With the help of the above-described aligning device, the parallel alignment of the connection pieces 5 which, after being fixed by means of the fixing screws 15 and after the anchoring head parts 6 and 7 are screwed in, give the latter the desired parallel alignment, can be brought about exceeding rapidly and precisely.

An industrially premanufactured inventive supraconstruction can be mounted on the parallel aligned connection pieces, as shown in FIG. 33. The supraconstruction 40, which is illustrated, is constructed of 5 elements; however, it can have any number of elements between 3 and 14. For the example shown, it is a component of the lower row of teeth 41 of a final set of teeth, which is illustrated in side view and the occlusion plane of which is indicated at 42. The supraconstruction 40 shown is a construction that is permanently connected with anchor head parts 7. It may also, however, have a removable construction.

The tooth elements 43 of the supraconstruction 40 are provided with receptacles in the form of conical boreholes 44, the center axes of which are aligned parallel to one another and perpendicularly to the occlusion plane 42. This construction simplifies the handling for the dentist and the dental technician. Because they are manufactured industrially, the conical crowns can be produced to fit accurately and to be advantageously priced. The expensive dental measurements become superfluous and the number of sessions with the patient are reduced.

I claim:

1. An anchor for a prosthetic superstructure which can be connected with an implant comprising a mounting part having threads engageable with the implant, a connecting piece supported on said mounting part for connecting with an anchor head for a dental prosthesis, said mounting part including a partial spherical space which accommodates the connection piece, said partial spherical space having a partial spherical wall, said mounting part further including a threaded passage and a threaded member threaded in said threaded passage and fixing the connecting piece on the mounting part in an aligned disposition.

2. An anchor for a prosthetic superstructure which can be connected with an implant comprising a mounting part having threads engageable with the implant, a connecting piece supported on said mounting part for connecting with an anchor head for a dental prosthesis, said mounting means including a threaded passage, a threaded member threaded in said threaded passage, said threaded member having an operable position fixing the connecting piece on the mounting part in an aligned disposition, said mounting part including a partial spherical space having an internal spherical surface, said connecting piece including a partial spherical portion having an external spherical surface, said partial spherical portion being received in said partial spherical space with said internal spherical surface mating with said external spherical surface, said partial spherical portion being precluded from moving relative to said partial spherical space when said threaded member is in said operable position.

3. An anchor for a prosthetic superstructure which can be connected with an implant comprising a mounting part having threads engageable with the implant, a connecting piece supported on said mounting part for connecting with an anchor head for a dental prosthesis, said mounting part including a partial spherical space which accommodates the connection piece, said partial spherical space having a partial spherical wall, said mounting part further including a threaded lateral passage, said passage having a conical end portion which intersects said spherical wall, and fixing means fixing the connecting piece on the mounting part in an aligned disposition, said fixing means including a threaded member in said passage.

4. An anchor for a prosthetic superstructure according to claim 3 wherein said conical end portion has an imaginary apex which is disposed within said partial spherical space.

5. An anchor for a prosthetic superstructure according to claim 3 wherein said threaded member has a conical end section which is adapted to be disposed substantially flush with the conical end portion of said passage.

6. An anchor for a prosthetic superstructure according to claim 3 wherein said connecting piece has a spherical portion received in said spherical space of said mounting part, said spherical portion having a threaded passageway which threadedly receives said anchor head of said dental prosthesis.

7. An anchor for a prosthetic superstructure which can be connect ed with an implant comprising a mounting part having threads engageable with the implant, a connecting piece supported on said mounting part for connecting with an anchor head for a dental prosthesis, and fixing means having a first operable position and a second operable position, said fixing means when in said first operable position permitting relative movement between said connecting piece and said mounting part, said fixing means when in said second operable position fixing the connecting piece on the mounting part in an aligned disposition, said mounting part including a partial spherical space having an internal spherical surface, said connecting piece including a partial spherical portion having an external spherical surface, said partial spherical portion being received in said partial spherical space with said internal spherical surface mating with said external spherical surface, said partial spherical portion being moveable in said partial spherical space when said fixing means is in said first operable position, said partial spherical portion being precluded from moving relative to said partial spherical space when said fixing means is in said second operable position, said fixing means including a threaded passage in said mounting piece and a threaded member in said threaded passage, said threaded passage opening up into said partial spherical space, said threaded member engaging said partial spherical portion of said connecting piece when said fixing means is in said second operable position.

8. An anchor for a prosthetic superstructure which can be connected with an implant comprising a mounting part having threads engageable with the implant, a connecting piece supported on said mounting part for connecting with an anchor head for a dental prosthesis, and fixing means having a first operable position and a second operable position, said fixing means when in said first operable position permitting relative movement between said connecting piece and said mounting part, said fixing means when in said second operable position fixing the connecting piece on the mounting part in an aligned disposition, said mounting part including a partial spherical space having an internal spherical surface, said connecting piece including a partial spherical portion having an external spherical surface, said partial spherical portion being received in said partial spherical space with said internal spherical surface mating with said external spherical surface, said partial spherical portion being moveable in said partial spherical space when said fixing means is in said first operable position, said partial spherical portion being precluded from moving relative to said partial spherical space when said fixing means is in said second operable position, said partial spherical space being greater than a hemispherical space to thereby retain said partial spherical portion of said connecting piece in said partial spherical space.

9. Aligning apparatus for aligning a plurality of connecting pieces in which each connecting piece is supported on a mounting part and each mounting part is supported on a dental implant comprising a generally flat aligning template having at least one slot, said template having upper and lower parallel aligning surfaces, an aligning structure engageable with said upper and lower aligning surfaces, said aligning structure including an aligning pin supported on each of said connecting pieces, said aligning pin extending through said at least one slot, said aligning structure being operable to align said aligning pins generally parallel to one another, said aligning template comprising two arc-shaped halves which are generally shaped like a person's jaw, and pivot means pivotable connecting said two arc-shaped halves.

10. Aligning apparatus according to claim 9 wherein said pivot means includes a handle, said handle being moveable relative to said two arc-shaped halves.

11. Aligning apparatus according to claim 9 wherein said pivot means includes a clamping sleeve disposed about a swiveling pin and an externally threaded bushing mounted on said clamping sleeve to preclude relative rotary movement between said bushing and said clamping sleeve, and an adjustable nut threadedly engaging said externally threaded bushing.

12. Aligning apparatus according to claim 9 wherein said template has two of said slots, said two slots each being elongate slots, each of said two arc-shaped halves having one of said slots.

13. Aligning apparatus for aligning a plurality of connecting pieces in which each connecting piece is supported on a mounting part and each mounting part is supported on a dental implant comprising a generally flat aligning template having at least one slot, said template having upper and lower parallel aligning surfaces, an aligning structure engageable with said upper and lower aligning surfaces, said aligning structure including an aligning pin supported on each of said connecting pieces, said aligning pin extending through said at least one slot, said aligning structure being operable to align said aligning pins generally parallel to one another, said aligning structure comprising a lower parallelizing part having an upper side disposable in an aligning position in which said upper side of said lower parallelizing part abuts said lower side of said aligning template in a parallel relationship, said aligning structure comprising an upper parallelizing part having a lower side disposable in an aligning position in which said lower side of said upper parallelizing part abuts said upper side of said aligning template in a parallel relationship, a clamping sleeve extending into said upper and lower parallelizing parts, said aligning pins being disposed in said clamping sleeve, and clamping means for clamping said upper and lower paralielizing parts in said respective aligned positions.

14. Aligning apparatus according to claim 13 wherein said upper parallelizing part has a central lower projection which projects into said slot in said aligning template, said upper parallelizing part having an upper part having a width in a direction parallel to said aligning template, said slot having a width less than the width of said upper part of said upper parallelizing part.

15. Aligning apparatus according to claim 13 wherein said clamping sleeve has a lower longitudinal end portion formed as a stop, said stop being engageable with said lower parallelizing part.

16. Aligning apparatus according to claim 15 wherein said stop has a conical configuration.

17. Aligning apparatus according to claim 15 wherein said clamping sleeve is provided with partial longitudinal slots which open up to the lower longitudinal end portion of the clamping sleeve.

18. Aligning apparatus according to claim 13 wherein said clamping sleeve and said upper and lower parallelizing parts have locking portions which preclude relative rotation between the clamping sleeve and the upper and lower parallelizing parts.

19. Aligning apparatus according to claim 13 wherein said clamping sleeve has longitudinally aligned projections, said upper and lower parallelizing parts having longitudinally extending grooves which receive said projections to thereby preclude relative rotation between said clamping sleeve and said upper and lower parallelizing parts.

20. Aligning apparatus according to claim 13 wherein said aligning pins have axes which are generally parallel to one another when said upper and lower parallelizing parts are in said aligned position.

21. A method of aligning a plurality of connecting pieces which are mounted on mounting parts fixed to dental implants comprising the steps of:

mounting each connecting piece on a mounting part such that each connecting piece is moveable relative to the mounting part;

providing a flat template having a slot;

adjusting the positioning of said template by providing said template in two relatively moveable halves, adjusting said two halves to an adjusted position and securing said two halves in said adjusted position;

mounting elongated mounting pins on each of said connecting pieces such that said mounting pins extend through said slot in said template.

* * * * *